United States Patent [19]

Keirns et al.

[11] 4,227,398
[45] Oct. 14, 1980

[54] PIEZOELECTRIC GUM MEASUREMENT DEVICE

[75] Inventors: Mary H. Keirns, Edison; Robert S. Lunt, III, N. Plainfield, both of N.J.

[73] Assignee: Exxon Research & Engineering Co., Florham Park, N.J.

[21] Appl. No.: 48,501

[22] Filed: Jun. 14, 1979

[51] Int. Cl.³ .................... G01N 5/04; G01N 33/22
[52] U.S. Cl. ................................. 73/61 R; 73/61.3
[58] Field of Search ............... 73/61R, 61.1 R, 61.3, 73/61.1 C, 23, 28, 29, 30

[56] References Cited

U.S. PATENT DOCUMENTS

| | | |
|---|---|---|
| 2,505,370 | 4/1950 | Sykes . |
| 3,164,004 | 1/1965 | King, Jr. ............... 73/23 |
| 3,253,219 | 5/1966 | Littler . |
| 3,260,104 | 7/1966 | King, Jr. ............... 73/23 |
| 3,266,291 | 8/1966 | King, Jr. ............... 73/23 |
| 3,427,864 | 2/1969 | King, Jr. ............... 73/29 |
| 3,561,253 | 2/1971 | Dorman ............... 73/28 |
| 3,653,253 | 4/1972 | Olin ............... 73/28 |
| 3,856,466 | 12/1974 | Crawford ............... 73/23 X |
| 3,863,495 | 2/1975 | Schulz et al. ............... 73/61.1 C |

OTHER PUBLICATIONS

King, Jr., W. H. *Using Quartz Crystals as Sorption Detectors-part 1*, in Research/Development pp. 28-34, Apr. 1969.

King, Jr., W. H. *Using Quartz Crystals as Sorption Detectors-part 2*, in Research/Development pp. 28-33, May 1969.

Primary Examiner—Daniel M. Yasich
Assistant Examiner—Joseph W. Roskos
Attorney, Agent, or Firm—Eugene Zagarella, Jr.

[57] ABSTRACT

An improved apparatus for measuring high-boiling components and particularly existent gum levels in aviation fuel comprising: a piezoelectric crystal, a lipophobic coating applied to the crystal for controlling sample location, a supply device for applying a sample to the crystal, a heater for heating the sample on the crystal, an evacuator, an oscillator associated with the crystal for measuring the resonant frequency thereof and an insulated housing for the crystal and heater.

10 Claims, 3 Drawing Figures

PIEZOELECTRIC GUM MEASUREMENT DEVICE

BACKGROUND OF THE INVENTION

This invention relates to an improved apparatus for measuring high boiling components found in liquid streams and particularly existent gum levels found in aviation fuels.

A variety of methods has been used in the analysis of petroleum hydrocarbons including gas chromatography, mass spectrometry, infrared spectrometry, ultraviolet spectrometry, X-ray analysis including X-ray fluorescence, X-ray diffraction and X-ray absorption, and electron microscopy. A number of different instruments have been developed using one or more of these or other methods.

Historically, existent gum (evaporation residue) levels in aviation fuel have been measured because there tends to be a relationship between the levels of existent gum and fuel purity. An increase in these gum levels from the refinery certification level usually means product contamination has occurred and the fuel may contain an unacceptable amount of "heavy ends".

The current technique for measuring existent gum in fuels is the steam jet method described in ASTM D381-70. In this method a measured quantity of fuel is evaporated under controlled conditions of temperature and flow of air or steam. The resulting residue in aviation gasoline and aircraft turbine fuel is weighed and reported as milligrams per 100 ml while for motor gasoline, the residue is weighed before and after extracting with n-heptane and the results reported in milligrams per 100 ml. While this method does provide an adequate and reliable determination of existent gum levels in fuels, it is somewhat cumbersome and inconvenient to run since it involves relatively large pieces of equipment requiring substantial capital investment as well as needing technically skilled personnel to carry out. Because of this, the test generally cannot be performed at individual field locations or terminals but at a central laboratory which involves the added cost of space and storage as well as a loss of time.

Accordingly, there is a need for a simplified, quicker and less complicated technique for measuring existent gum levels in fuels which will require less burdensome apparatus with respect to size and investment. The availability of such a technique and apparatus will permit testing at various locations in the field rather than at a central laboratory and therefore ease the problem of determining off spec quality and allow for quicker correction of such problem at a considerable saving of time and cost.

The use of piezoelectric crystals for the selective analyses of fluid mixtures has been known in the art for some time. The basic principle involved in using a piezoelectric crystal as a detection device involves measuring the mass change of a vibrating crystal. There are two modes in which the crystal is employed. Most involve the use of a predeposited substrate on the crystal to absorb the material to be analyzed. As the substrate or coating of the crystal interacts with another material and thus changes weight, the change in weight or mass can be detected and used for determining qualitatively and quantitatively various components present. One of the early patents which disclosed coated piezoelectric analyzers is U.S. Pat. No. 3,164,004 by William H. King, issued Jan. 5, 1965. Another application of this technique is disclosed in U.S. Pat. No. 3,427,864 by William H. King, issued Feb. 18, 1969, wherein the presence of moisture in the fluid mixture is detected using a piezoelectric crystal coated with a deliquescent salt such as lithium chloride. A variation of this technique is disclosed in U.S. Pat. No. 3,260,104, issued July 12, 1966, and U.S. Pat. No. 3,266,291, issued Aug. 16, 1966, both by William H. King, which show an analyzer having two detection devices both having a piezoelectric crystal, one of which has a substrate selective to a particular material, and the other acting as a reference. The net output of the two detection devices is a measure of the interaction of at least one component to be detected.

Another method of using piezoelectric crystals as detection devices involves applications where the crystal is not coated with a substrate. This generally involves depositing a material mixed in solvent or other carrier on the crystal, evaporation of the carrier leaving behind the material of interest followed by measurement of crystal frequency. Applications of this type have been disclosed in U.S. Pat. No. 3,856,466, issued on Dec. 24, 1974 to Harry M. Crawford, and U.S. Pat No. 3,863,495, issued on Feb. 4, 1975 to Wolfgan Schultz et al.

In the above-described techniques of using piezoelectric crystals, the sample location is dependent in the first instance on the substrate coating amount and dimensions and the makeup of the surrounding materials while in the second instance it is dependent on the particular technique of sample application and control thereof.

Despite the longstanding use of piezoelectric crystals in detection devices as illustrated in the above-noted patents, there still is the need for an apparatus and technique wherein sample location is readily controlled resulting in quick, accurate and consistent measurements of high-boiling components in liquids, particularly existent gum levels in fuels. More particularly, there is a need for a simplified, portable type apparatus useful in measuring gum levels in fuels in a quick manner at convenient locations.

SUMMARY OF THE INVENTION

This invention provides an apparatus for measuring high-boiling components found in liquid streams in a simplified, quick, accurate and consistent manner. This apparatus comprises piezoelectric crystal means, a lipophobic coating applied to said crystal means for controlling sample location, means for applying a sample to said crystal, heater means for heating said sample, evacuation means, oscillator means associated with said crystal for measuring the resonant frequency thereof and insulated housing means for said crystal and heater.

BRIEF DESCRIPTION OF THE DRAWINGS

The instant invention may be better understood by reference to the accompanying drawings wherein.

DETAILED DESCRIPTION OF THE INVENTION

Figure 1:
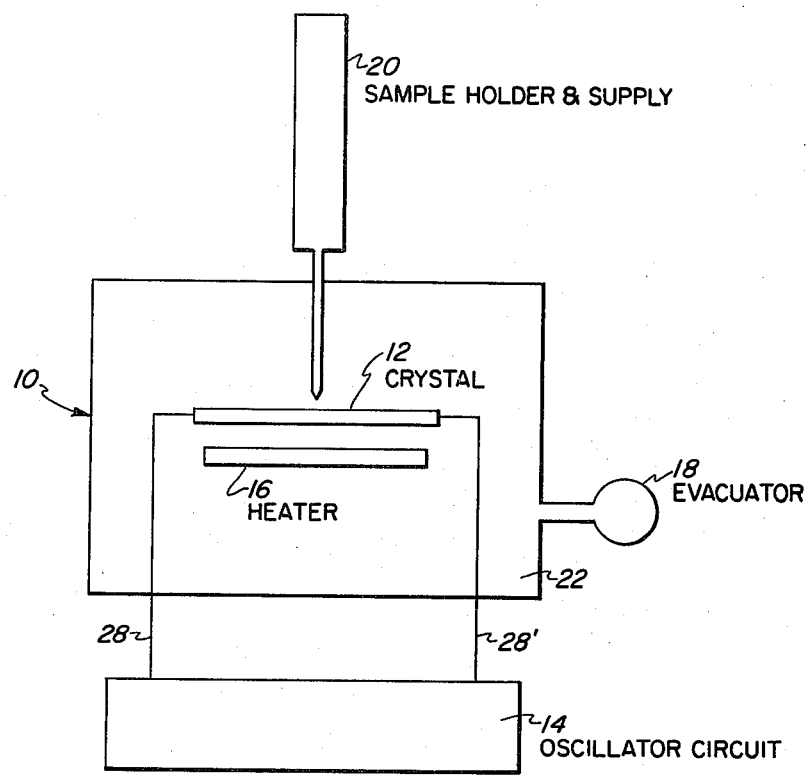
FIG. 1 illustrates schematically the overall arrangement of the apparatus according to the present invention.

In FIG. 1, the detector apparatus of this invention is disclosed. The detector, generally indicated at 10, comprises a light weight portable type apparatus. The apparatus includes a piezoelectric crystal 12 with an oscillator circuit 14, a heater 16, an evacuator 18, a sample holder and supplier 20, lead wires 28 and 28' and an insulated housing unit 22.

Figure 2:
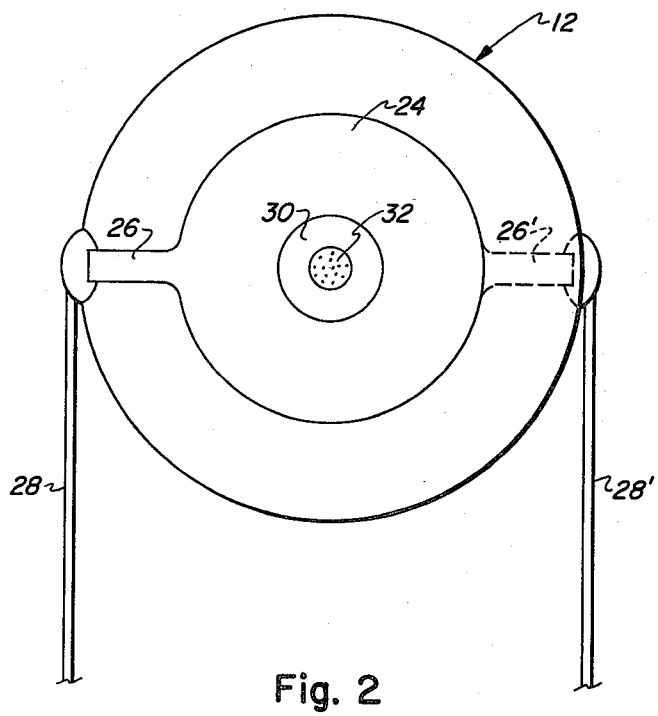
FIG. 2 illustrates one embodiment of the piezoelectric crystal with lipophobic coating according to the present invention.

FIG. 2 illustrates a piezoelectric crystal as used in this apparatus. The crystal designated generally as 12 has a circular electrode 24 placed upon its surface which is connected by narrower conducting strips 26 and 26' on either side to external leads 28 and 28'. The crystal 12 has a lipophobic coating 30 which accurately defines the sample area and confines the sample 32 to an area on the crystal.

The apparatus of this invention provides for a simplified and quick technique for measuring high-boiling components in fuels and particularly allows for results which are quite accurate. In prior art analyzers which use crystals coated with a substrate for absorbing material, the amount of substrate is a significant variable and its volume, thickness, weight and location on the responsive crystal material are of significance in determining the response of the detector. U.S. Pat. No. 3,856,466 referred to above discloses apparatus using a noncoated crystal and indicates the importance of disposing samples in the center of the crystal and in the same relative positions thereon.

The use of the apparatus of this invention overcomes many of the problems associated with the earlier type analyzers and furthermore provides a relatively simple, yet accurate and quick technique for measuring high-boiling components in fuels. One significant advantage of this apparatus is its ready accessibility which allows for measurement at convenient locations in the field.

The piezoelectric crystal used in this invention may be any responsive material which exhibits piezoelectric properties. The material exhibits piezoelectric properties if when subject to an electrical potential it mechanically deforms and vice versa, when subject to a mechanical pressure it develops an electrical potential. Several such materials are known; for example, crystals such as quartz, tourmaline Rochelle salts, barium titanate ceramic compositions, lead metaniobates, lead zirconate-lead titanates and the like. Quartz is the particular crystal most often employed in electrical applications, but the instant invention is not to be limited thereto.

The frequency at which a piezoelectric material, such as a quartz crystal, oscillates is dependent on several variables. These include the thickness of the crystal, the electrode structure, the characteristics of the oscillating circuit to which the crystal is connected, the temperature, and in the case of crystals, the particular axis along which it is cut. The frequency, however, changes with corresponding change in the mass of the electrode. The slightest change in the electrode mass of an AT cut piezoelectric crystal will produce a detectable change in its resonant frequency. Thus, it is generally accepted that a piezoelectric detecting circuit can detect a weight addition to the electrode surface of as little as $10^{-13}$ to $10^{-9}$ grams. Generally, piezoelectric crystals having a resonance frequency in the range of 9 MHz are suitable for use in this invention.

The piezoelectric crystal 12 includes two electrodes 26 and 26' suitably bonded to the crystal. Each electrode, as illustrated in FIG. 2, is connected electrically to the electrical connecting means or leads 28 and 28', and comprises a metallic coating. Preferably the metal used has high electrical conductivity and in a preferred embodiment may comprise gold in contact directly with the quartz and a nickel coating over the gold to make the exposed surface resistant to abrasion such as one might encounter in use. These electrode leads permit the vibrational frequency of the crystal to be measured by an external oscillator circuit 14 shown in FIG. 1.

As indicated earlier, it is recognized that samples should generally be placed on the crystal in the same position so as to obtain consistent and comparable frequencies. It has been found that the sensitivity of the crystal to mass changes decreases as a cosine function of electrode radius, reaching zero at the edge of the crystal. In order to get accurate and repeatable test results and to simplify the placement of the sample in the desired position of the crystal, the crystal of this invention has a lipophobic coating deposited on it in such a way as to confine the sample to the center of the crystal. This is generally accomplished by forming a ring of the lipophobic material around the center in a manner illustrated by FIG. 2. By forming such a ring, the sample will be repelled if it moves outside of the defined central area and thus will be confined to the desired area. The ring size may vary and to some extent will be limited by the technology available to custom coat the crystals. Generally a ring size of up to about 0.40 inches, preferably up to about 0.33 inches and more preferably up to about 0.3 inches inner diameter is utilized.

In addition to the use of a ring-type coating as an alternative, the crystal may receive a solid thin coating of the lipophobic material and a sample applied to the center of this so-coated crystal will tend to bead up in a mass at the crystal center. Generally the lipophobic coating which is used in either the solid or ring-type applications will be a thin film of sufficient thickness that the sample material will not spread but rather bead up in a mass and still allow the crystal to oscillate. More particularly, the coating will generally be of a thickness of up to about 0.001 inches.

The lipophobic or repellant material that is used may be any substance which will adhere to the electrode and will repel the liquid sample. Additionally, it should resist removal by the washing fluid or solvent that is used to remove the samples. Generally, materials of this type are those that repel fats or similar substances. Such materials include, for example, Teflon, silicones, olefinic polymers, etc. with Teflon being particularly preferred.

The electronic circuitry necessary for operation of the apparatus of this invention includes an oscillator circuit which obtains the resonant frequency from a crystal containing sample material. The oscillator circuit produces a radio frequency signal, usually about 9 to 27 megahertz, which can be converted to an audio frequency signal and which in turn can be transmitted to a standard frequency converter. The converter changes the audio frequency signal into an analog or digital signal and such analog or digital signal is transmitted to an output circuit in either analog or digital form and more commonly the output comprises an analog signal which manifests itself as a needle indicator of a conventional microammeter meter. By converting the audio frequency signal, the converter thereby emits a signal which is available for reading with a frequency counter at the output.

It should be appreciated that the oscillator circuits employed in the instant invention are well known in the art and obviously, various suitable standard oscillator circuits may be employed. It should be emphasized that the particular type of oscillator circuit with which the crystal is connected is not critical. Well-known oscillators which may be used include the Hartley oscillator and its many modifications, the tuned grid-tuned plate oscillator, the Dynatron oscillator, the transition oscillator and many other forms of feedback oscillators. Similarly the converters and counters used in the circuit are well known in the art and thus any of such known units may be employed in the present invention.

In order to evaporate the liquid or jet fuel from the crystal, a heater of the resistance type is placed in close proximity to the crystal. Generally the voltage of the heater will be placed at a level to provide adequate heat to evaporate the fuel but not so much as to make the crystal unstable or fail to resonate.

One particular feature of this invention is the use of an evacuator or vacuum pump to aid in the process. This not only helps speed up the evaporation of the sample but it has been found that such means allows the operation to be conducted at a lower temperature, shortens the time needed to conduct the test and gives better, more accurate results. A variety of vacuum pumps, many of which are conventional and commercially available, may be used in this invention.

The sample is supplied or placed on the crystal through a sample holder or supply device 20 as shown in FIG. 1. Generally, a variety of sample supply means may be used and more particularly, a syringe or needle-type apparatus with a tube for holding sample can be used. The apparatus is adapted with opening means so that the sample supply means can be placed in the same position relative to the crystal each time a new sample is being added. A suitable holding means, not shown, may be attached to the detector device 10 to hold the sample supply means 20 in place.

A housing unit 22, which is preferably a machine metal plate having a plurality of openings is provided to house the crystal and heater means. This housing unit is preferably insulated and adapted to maintain a vacuum as applied during the operation of the test procedure.

Other apparatus may be employed in this invention including, for example, timer means and an aspirator and charcoal canister.

In operation the instant invention involves first cleaning a crystal with solvent such as chloroform and acetone and then placing the cleaned crystal into the device and allowing to dry.

The crystal is calibrated using a number of fuels having known gum levels such as fuels with added contaminants. It is necessary, of course, to select fuels as standards which will cover the range of frequency expected for the fuels to be tested. A measured amount of standard fuel sample, i.e. 10 ul, is applied to the crystal using the syringe device illustrated in FIG. 1.

Figure 3:
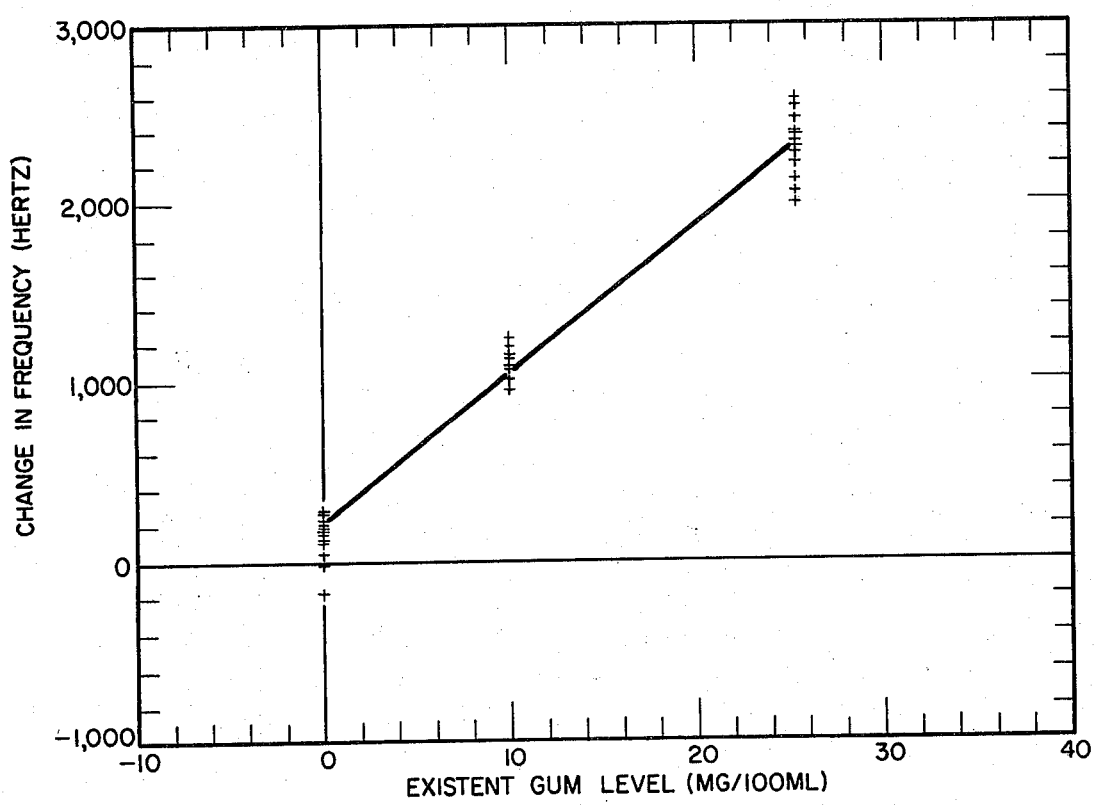
FIG. 3 is a graphical illustration of frequency change versus gum level in mg./100 ml.

A plot (FIG. 3) of resulting frequency change vs. extent gum level is made for the fuels with known gum levels, i.e. jet fuel doped with 0, 200 and 500 ppm Bright Stock (about 0, 10 and 25 mg/100 ml respectively), using an average of two determinations for each point with the resulting calibration line being fitted to the data using the method of least squares. Frequency change is the difference between the frequency of the clean crystal (without sample) and the frequency of the crystal with sample thereon. A sample of test fuel is then placed in a like manner in the apparatus, and the resulting change in frequency determined. Using the predetermined calibration plot (FIG. 3), the amount of existent gum can then be established. For example, a test sample showing a frequency change of about 1200 hertz would have an existent gum level of about 11.9 mg/100 ml using predetermined calibration plot, FIG. 3.

What is claimed is:

1. An apparatus for measuring high boiling point components and gum present in a liquid stream comprising:
   (a) piezoelectric crystal means;
   (b) a lipophobic coating applied to said crystal means for controlling sample location;
   (c) means for applying a sample to said crystal;
   (d) heater means for heating sample on said crystal;
   (e) oscillator means associated with said crystal for measuring the resonant frequency thereof;
   (f) evacuator means; and
   (g) insulated housing means for said crystal and heater.

2. The apparatus of claim 1 wherein said lipophobic coating is applied to said crystal in the form of a ring about the center of the crystal to confine the sample to the center thereof.

3. The apparatus of claim 2 wherein said ring has an inner diameter of up to about 0.40 inches.

4. The apparatus of claim 3 wherein said lipophobic coating material is selected from the group consisting of Teflon, silicones and olefinic polymers.

5. The apparatus of claim 4 wherein said ring has an inner diameter of up to about 0.33 inches.

6. The apparatus of claim 5 wherein said crystal is made of quartz.

7. The apparatus of claim 6 wherein said lipophobic coating material is Teflon.

8. The apparatus of claim 1 wherein said lipophobic coating is applied to said crystal in the form of a solid thin film having sufficient thickness such that a sample material deposited thereon will not spread but rather bead up in a mass and still allow said crystal to oscillate.

9. The apparatus of claim 8 wherein said lipophobic coating material is selected from the group consisting of Teflon, silicones and olefinic polymers.

10. The apparatus of claim 9 wherein said crystal is made of quartz and said lipophobic coating material is Teflon.

* * * * *